United States Patent
Williams

(10) Patent No.: US 9,750,397 B2
(45) Date of Patent: Sep. 5, 2017

(54) MECHANISM OF SMALL DRIVE WIRE RETENTION ON SPOOL

(71) Applicant: Cook Medical Technologies LLC, Bloomington, IN (US)

(72) Inventor: Michael Lee Williams, Pinnacle, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 110 days.

(21) Appl. No.: 14/722,737

(22) Filed: May 27, 2015

(65) Prior Publication Data

US 2015/0366435 A1 Dec. 24, 2015

Related U.S. Application Data

(60) Provisional application No. 62/014,879, filed on Jun. 20, 2014.

(51) Int. Cl.
| | |
|---|---|
| *A61B 1/00* | (2006.01) |
| *A61M 25/00* | (2006.01) |
| *A61B 17/00* | (2006.01) |
| *A61B 1/005* | (2006.01) |
| *F16C 1/12* | (2006.01) |
| *A61M 25/01* | (2006.01) |

(52) U.S. Cl.
CPC .......... *A61B 1/0057* (2013.01); *A61B 1/0052* (2013.01); *A61M 25/0136* (2013.01); *F16C 1/12* (2013.01); *A61M 25/0147* (2013.01); *Y10T 74/2042* (2015.01); *Y10T 74/20372* (2015.01)

(58) Field of Classification Search
CPC .... A61B 2017/003; A61B 2017/00305; A61B 2017/00309; A61B 2017/00314; A61B 2017/00318; A61B 2017/00323; A61B 2017/00327; A61B 2017/00331; A61M 25/0133; A61M 25/0136; A61M 25/0138; A61M 25/0141; A61M 25/0144; A61M 25/0147
USPC ................ 600/139–152; 604/528; 606/1
See application file for complete search history.

(56) References Cited

U.S. PATENT DOCUMENTS

| | | | |
|---|---|---|---|
| 3,897,775 A | 8/1975 | Furihata | |
| 5,413,107 A | 5/1995 | Oakley et al. | |
| 7,922,650 B2 | 4/2011 | McWeeney et al. | |
| 2005/0054899 A1* | 3/2005 | Miyake ................ | A61B 1/0052 600/152 |

(Continued)

FOREIGN PATENT DOCUMENTS

JP 2006116151 A * 5/2006 ........... A61B 1/0052

*Primary Examiner* — Ryan Henderson
(74) *Attorney, Agent, or Firm* — Brinks Gilson & Lione

(57) ABSTRACT

A steering mechanism for a medical device that is configured for passing through the body cavities of a patient and for passage through an endoscope working channel is described. The mechanism comprises at least one spool having a central hole through which a central axle passes, the spool being rotatable about the axle, and the spool having at least one retaining tube having a lumen therethrough and configured to contain a portion of a drive cable. The drive cables, which may include UHMWPE, are capable of and are effective for deflecting the distal end of a catheter or endoscopic device, while preferably each being at least partially disposed through a retaining tube that is effective to prevent tangling or other binding of the cable(s).

9 Claims, 12 Drawing Sheets

(56) References Cited

U.S. PATENT DOCUMENTS

2012/0265215 A1* 10/2012 Durant ................ A61B 1/0055
606/130
2014/0121462 A1* 5/2014 Okamoto ............. A61B 1/0052
600/149

* cited by examiner

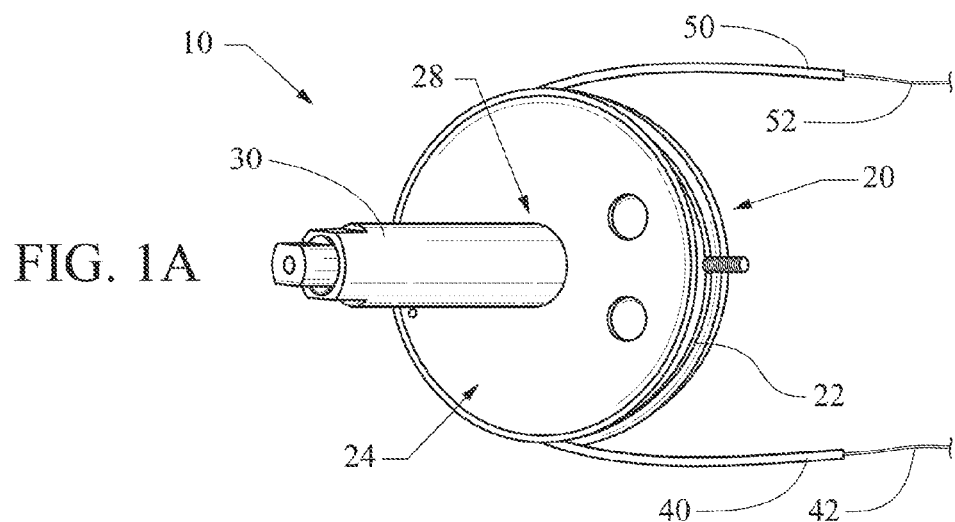
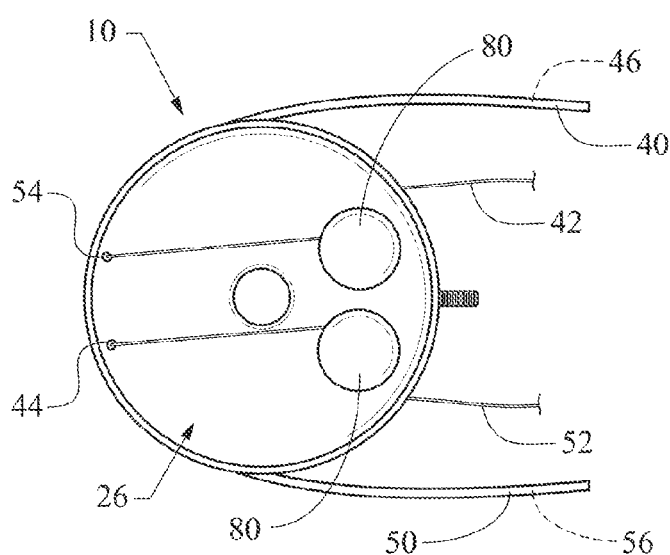
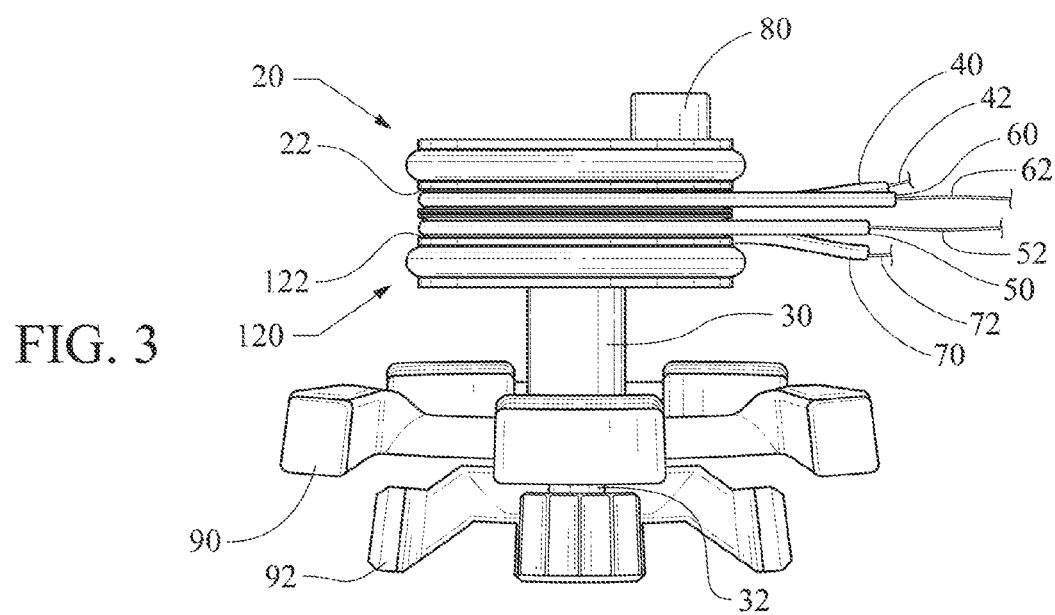

MECHANISM OF SMALL DRIVE WIRE RETENTION ON SPOOL

CROSS-REFERENCE TO RELATED APPLICATIONS

This application claims priority to U.S. Provisional Application Ser. No. 62/014,879, filed Jun. 20, 2014, which is incorporated herein by reference in its entirety.

BACKGROUND

Technical Field

Embodiments of the present invention relate to medical devices. More particularly, embodiments disclosed herein relate to a steering mechanism for a deflectable catheter or endoscope for insertion into a lumen of a body vessel.

Background

Steerable catheters and endoscopic devices, in which a handle containing a steering mechanism is held outside of the body of a patient undergoing treatment or observation is used to control the distal tip of an elongate body of a medical device as it moves through the body cavities of the patient, are known. However, it has been a challenge to develop a steering mechanism with a spool or series of spools that is capable of, and preferably is effective for, preventing slippage of the drive cables which can transmit sufficient force to the distal end of the device within a relatively low-profile handle. Described herein is a steering mechanism having several features, which allow for drive wire retention on the spool or spools.

BRIEF SUMMARY

One embodiment includes a steering mechanism for a medical device, the medical device having a circumference, a proximal end, and a distal end. The steering mechanism comprises a first central axle having a first longitudinal axis and a second central axle having a second longitudinal axis. The mechanism further comprises a first spool having a first diameter and a first circumferential edge. The first central axle of the steering mechanism is disposed centrally on or through the first spool. The first spool is rotatable about the first central axle. The mechanism also comprises a second spool having a second diameter and a second circumferential edge. The second central axle of the steering mechanism is disposed centrally on or through the second spool, the second spool being rotatable about the second central axle. The mechanism comprises a first retaining tube having a first lumen therethrough; a first length; a first midpoint; and a first and second end. The first retaining tube is attached along a portion of its length inclusive of the first midpoint to a portion of the first circumferential edge of the first spool. A first drive cable having two ends passes through and extends through the first lumen of the first retaining tube and beyond the first and second ends of the first retaining tube. The ends of the first drive cable extend toward the distal end of the medical device. The steering mechanism further comprises a second retaining tube having a second lumen therethrough; a second length; a second midpoint; and a third and fourth end. The second retaining tube is attached along a portion of its length inclusive of the second midpoint to a portion of the second circumferential edge of the second spool. A second drive cable having two ends passes through and extends through the second lumen of the second retaining tube and beyond the third and fourth ends of the second retaining tube. The ends of the second drive cable extend toward the distal end of the medical device. A first steering element is attached to the first spool and rotatable therewith. A second steering element is attached to the second spool and rotatable therewith. The first spool and the second spool are rotatable independent of one another.

In another embodiment, a steering mechanism for a medical device is provided. The medical device has a circumference, a proximal end, and a distal end. The steering mechanism comprises a first central axle having a first longitudinal axis and a second central axle having a second longitudinal axis. The mechanism comprises a first spool having a first diameter and a first circumferential edge. The first central axle of the steering mechanism is disposed centrally on or through the first spool. The first spool is rotatable about the first central axle. The steering mechanism comprises a second spool having a second diameter and a second circumferential edge. The second central axle of the steering mechanism is disposed centrally on or through the second spool. The second spool is rotatable about the second central axle. A first retaining tube having a first lumen therethrough; a first length; a first midpoint; and a first and second end is provided. The first retaining tube is attached along a portion of its length inclusive of the first midpoint to a portion of the first circumferential edge of the first spool. A first drive cable passes through the first end of and into the first lumen of the first retaining tube. A second drive cable passes through the second end of and into the first lumen of the first retaining tube. The first drive cable and second drive cable have distal drive cable ends which extend toward the distal end of the medical device. A second retaining tube having a second lumen therethrough; a second length; a second midpoint; and a third and fourth end is also provided in the steering mechanism. The second retaining tube being attached along a portion of its length inclusive of the second midpoint to a portion of the second circumferential edge of the second spool. A third drive cable passes through the third end of and into the second lumen of the second retaining tube. A fourth drive cable passes through the fourth end of and into the second lumen of the second retaining tube. The third drive cable and fourth drive cable have distal drive cable ends which extend toward the distal end of the medical device. A first steering element is attached to the first spool and rotatable therewith. A second steering element is attached to the second spool and rotatable therewith. The first spool and the second spool are rotatable independent of one another.

Further objects, features, and advantages of the present invention will become apparent from consideration of the following description and the appended claims when taken in connection with the accompanying drawings.

BRIEF DESCRIPTION OF THE DRAWINGS

FIGS. 1A-1D are perspective views of a spool and retaining tube;

FIG. 2 is a view of a spool and retaining tube;

FIG. 3 is a side view of a rotation element and spool having a retaining tube in accordance with another embodiment;

DETAILED DESCRIPTION

Figure 1B:
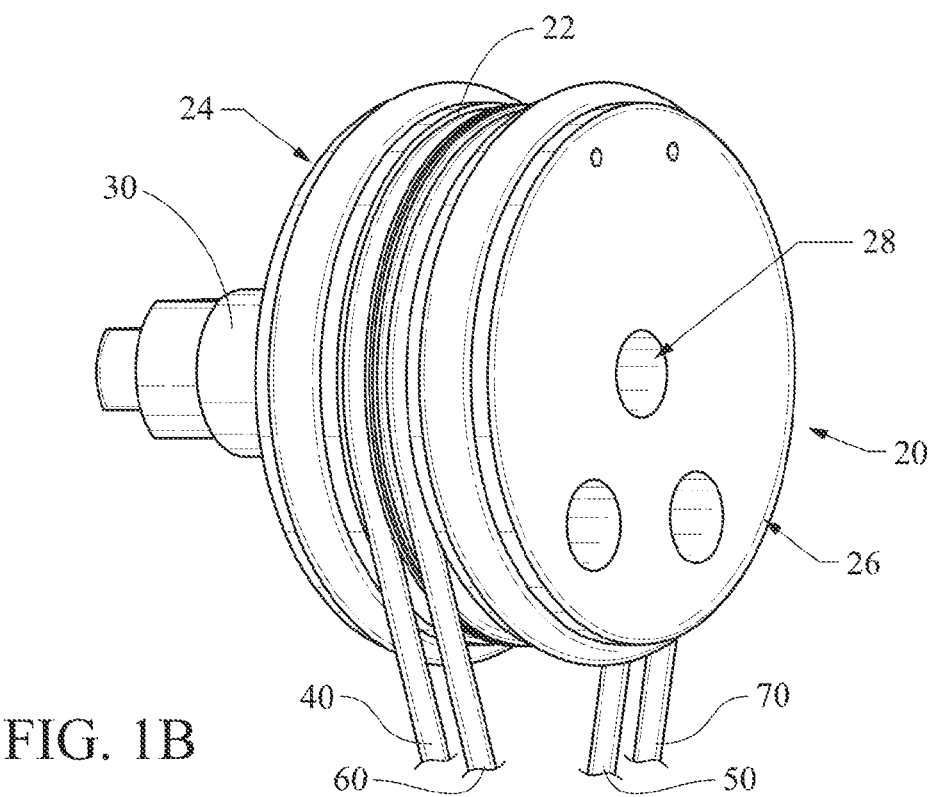
Figure 1C:
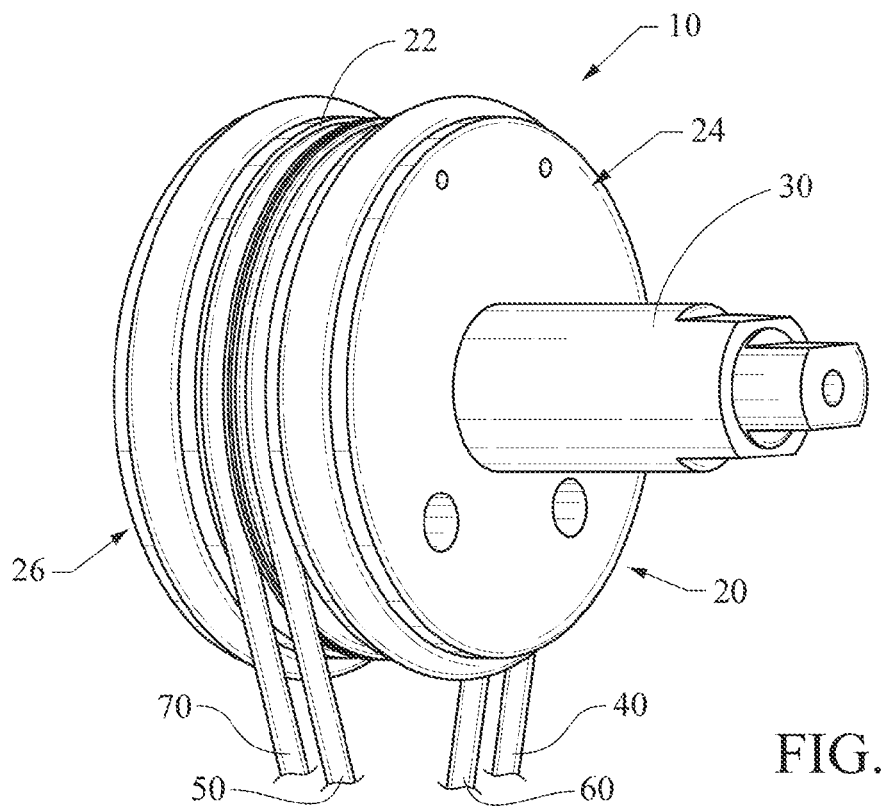
Figure 1D:
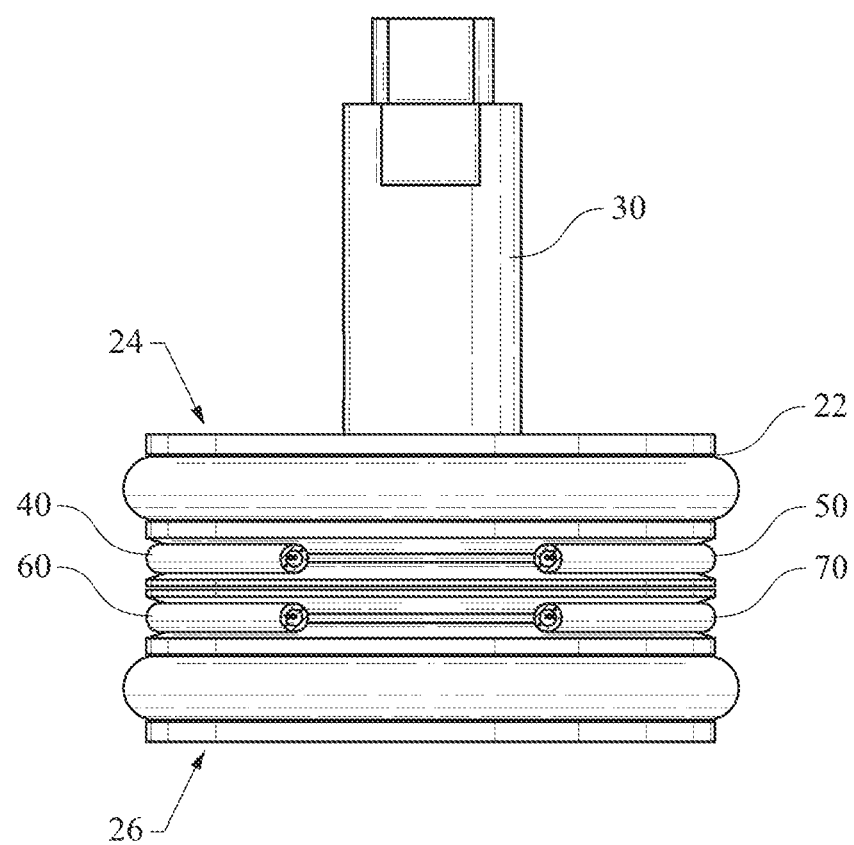

The description that follows is not intended to limit the scope of the invention in any manner, but rather serves to enable those skilled in the art to make and use the invention.

It is to be understood that the figures are schematic and do not show the various components to their actual scale. In many instances, the figures show scaled up components to assist the reader.

In this description, when referring to a device, a catheter, or endoscope, the term distal is used to refer to an end of a component which in use is furthest from the physician during the medical procedure, including within a patient. The term proximal is used to refer to an end of a component closest to the physician and in practice in or adjacent an external manipulation part of the deployment or treatment apparatus.

The terms "substantially" or "about" used herein with reference to a quantity includes variations in the recited quantity that are equivalent to the quantity recited, such as an amount that is equivalent to the quantity recited for an intended purpose or function.

A system for catheterization or endoscopy having a steering mechanism is described. The primary components of the system include an elongate catheter or endoscope (or combination of both), a hub, and a handle. The hub can be integral or permanently part of the catheter such that they together define a single catheter assembly. The hub may be joined to the catheter with injection molding or adhesive bonding. Alternatively, the hub can be integral with the handle. In another embodiment, the hub is not integral with the catheter or the handle but connects to these items with connectors, such as threaded connectors or other known connectors.

The catheter includes an elongated, cylindrical body that extends the entire length of the catheter. The catheter body has an outer diameter and may be constructed from any suitable material, such as PEBAX (polyether block amides), nylon, polytetrafluoroethylene (PTFE), polyethylene, polyurethane, fluorinated ethylene propylene (FEP), thermoplastic elastomers and the like, or combinations thereof. The body may be formed of a single material using known techniques in the art, such as extrusion, or multiple materials by joining multiple extruded sections by heat bonding, adhesive bonding, lamination or other known techniques.

In some applications, the catheter can have a varying degree of stiffness from the distal end towards the proximal end. The proximal end should be stiff enough for the device to advance in the tract to the desired location. The distal end should be soft enough to provide a reduction in trauma during insertion but rigid enough to provide adequate support during the procedure and prevent collapse or kinking.

The distal portion of the catheter may be made more flexible than the remainder of the catheter to allow for steerability of the catheter in vivo. This allows the catheter to be easily advanced without compressing and with minimal twisting while providing deflection capabilities to the distal portion for deflecting the distal end.

In another embodiment, the distal portion of the catheter may contain a preset curve detail that allows a physician to easily access various locations with minimal manipulation via passive deflection. Curves of various shapes and geometries may be preset to the distal portion of the catheter. For example, these curves may vary between 10 and 270 degrees from vertical, depending upon the specific application of the system. To insert the catheter, the curve should be such that when a dilator or stiff guidewire is inserted into a working channel of the catheter, the catheter is straight or nearly straight, but when the dilator or guidewire is removed, the distal portion reverts to the curved configuration providing access to a desired location. In other embodiments, mechanical joints or configurations may be utilized that allow the distal portion of the catheter to flex or bend in one or more directions more easily.

In one embodiment, the distal portion of the sleeve can have a radiopaque marker band mounted thereon to provide confirmation of the location of the distal end via fluoroscopy.

The catheter handle is suitable for steering a catheter shaft having a proximal region and a distal region and at least one steering wire having a distal end region secured at or near the distal end region of the catheter shaft and a proximal end. The catheter handle includes a catheter housing having the proximal end of the catheter shaft attached thereto and a steering controller carried by the catheter housing and having the proximal end of the at least one steering wire connected thereto. The steering controller is movable from a first position to a second position. The steering controller applies tension to the at least one steering wire when the steering controller moves from the first position to the second position. The catheter handle can further include a lock mechanism for retaining the steering controller in the second position to prevent movement thereof.

The body of the catheter can define at least one lumen or working channel that extends at least a portion of the length of the catheter and allows for the passage of various treatment or diagnostic devices, such as guide wires, retrieval baskets, lasers, biopsy forceps, steering drive wires, and so forth. The body of the catheter may also include additional channels for use, e.g., as irrigation/insufflation channels or additional working channels for one or more of the instruments mentioned above.

In one embodiment, the channels each extend the entire length of the catheter and allow the passage of devices, liquids and/or gases to and from the treatment area. In one embodiment, the catheter has eight lumens. The catheter may also include a channel for containing a fiberscope, fiber optic cables or other small diameter imaging devices. In an embodiment with eight lumens, for example, the lumens may comprise four lumens for drive cables, one for a camera, one for a light source, one to function as a fluid or flushing channel, and one as a working channel for the passage of devices therethrough. In one embodiment, an eight lumen device may have cable lumens with diameters of about 0.010 inch to about 0.012 inch (about 0.25 millimeters to about 0.31 millimeters).

The assembly also includes at least one control or steering wire, represented in the figures by drive cables 42/52/62/72. It may useful for such steering wires to be present in pairs arranged on opposite sides of the catheter to one another. In one embodiment, two pairs of steering wires 42/52 and 62/72, for a total of four steering wires, are present, arranged at intervals 90 degrees apart in the catheter body. The steering wires cause a distal portion of the catheter to deflect in one or more directions when pulled by the user. The steering wires are located on opposite sides of the catheter and can slide within grooves or dedicated channels or lumens on opposite sides of the catheter body. The grooves, channels, or lumens may be offset from the central, longitudinal axis of the catheter. The steering wires extend from the distal end of the catheter to the opposing, proximal end of the catheter, and may further extend into the hub.

The steering wires may be attached to the distal end of the catheter in any conventional manner, such as adhesive bonding, heat bonding, crimping, laser welding, resistance welding, soldering or other known techniques, at anchor points such that movement of the wires causes the distal end to deflect in a controllable manner. In one embodiment, the steering wires can be attached via welding or adhesive bonding to a fluoroscopy marker band fixedly attached to the distal end. In one embodiment, the band may be held in place via adhesive and/or an outer sleeve, as will be described in more detail below. The steering wires should have sufficient tensile strength and modulus of elasticity that they deform minimally or that they substantially do not deform (elongate) such that curved deflection is readily achieved.

Turning now to FIGS. 1A-D and 2, a portion of a steering mechanism 10 is illustrated. The single spool 20 of FIG. 1A has a center 28 and a hole formed or bored therethrough. The first central axle 30 passes through the center 28. The spool 20 has a first side 24 and a second side 26, and between these two opposite sides runs the circumferential edge or groove 22.

A first retaining tube can be seen attached to the circumferential edge or groove 22 of the spool 20. The first retaining tube is represented by first retaining tube half (or retention tube half) 40 and second retaining tube half 50. These tube halves have lumens formed therethrough, designated by numbers 46 and 56 respectively. A first drive cable 42 passes through at least a portion of the retaining tube half 40 and extends through its ends. A benefit of including retaining tubes in the steering mechanism is that the drive cables do not merely rest on the surface of the spool but are contained within an enclosed space. As a result, the drive cables will not slip off of the spool, thanks at least in part to the retaining tube. Because each drive cable is disposed at least partially through its own retaining tube half, the retaining tube structure also effectively prevents tangling of the drive cables with each other and/or with other components of the device.

After exiting the retaining tube 40, the first drive cable 42 may then pass into a dedicated drive wire lumen running through the catheter body, ultimately attaching to the distal end of the catheter or endoscope device. Manipulation of the wire through the rotational elements or steering wheels or knobs of the handle of the device then causes the distal end of the catheter to deflect.

A different view of the spool assembly is shown in FIG. 2. In this top-down view, one arrangement of the elements of the spool assembly can be seen. For example, the proximal or operator-facing end of second drive cable 52 is visible. The drive wire 52 passes through the lumen 56 of second retaining tube half 50 and exits the tube half at substantially the midpoint of the proximal end of the spool 20. At this point, the drive cable 52 is routed up to the first face 24 of spool 20 through skive 54 which has been formed or drilled through the spool 20. In one embodiment, the drive cables 42/52 can terminate at the knobs 80.

Figure 9:
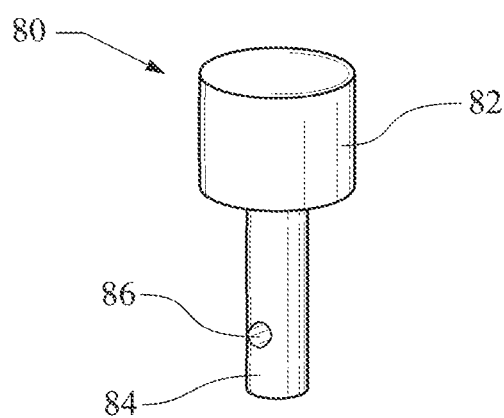
FIG. 9 is a schematic view of a knob.

As shown in FIG. 9, the knobs 80 can comprise a head 82 integral with a shank 84 which is driven into the first face 24 of spool 20. Optionally, the shank may include at least one hole 86 formed or drilled therethrough. The drive cables 42/52/62/72 can be attached to these knobs 80 in any suitable manner, including passing through the hole 86 and being knotted around the shank 84. In one embodiment the knobs 80 can be turned to produce a tension force on the drive cables 42/52/62/72 to best allow for force transmission to the distal end of the medical device. Following this, the assembly may be permanently sealed in order to prevent adjustment of the knobs 80. In another embodiment 80, the housing containing the steering mechanism may be opened by the user in order to adjust the tension on the drive cables 42/52/62/72. In either case, the knobs 80 may represent hexhead screws which are tightened by engaging a hex wrench to tighten the cables by rotation of the screws.

In one embodiment, the drive cables 42/52/62/72 are made of an ultra high molecular weight polyethylene (UHMWPE). UHMWPE is a material which is formed from monomers of ethylene which come together as polyethylenes and then are further treated until they have, in some embodiments, mean molecular weights ranging from two million to six million. Cables made from UHMWPE exhibit excellent toughness for a material having a small diameter and a low density. UHMWPE cables also tend not to slacken like a metal cable might. Moreover, UHMWPE cables are highly lubricious, and therefore slide well along adjacent surfaces, such as the walls of a wire lumen of a catheter. Therefore, UHMWPE cables are well-suited to passage through small lumens.

The high lubricity of the UHMWPE cables also means that slippage of the drive cable, for instance off of the surface of a rotating spool, is also a risk. Passing the cables through a retaining tube that is affixed to the spool is a way of mitigating this risk.

In one aspect, the UHMWPE cables may be configured as braids or unbraided strands including at least one strand (which also includes a plurality of strands whether braided or not). The UHMWPE cables may be present in any configuration, but braided cables are advantageously small in diameter while having increased pulling strength and provide for excellent transmission of force. Thus, a number of UHMWPE strands may be braided together to form a cable of slightly larger diameter but having better tensile strength. Braided steering wires 42/52/62/72 may be considered for any embodiment of the present steering mechanism as described herein. The braided steering wires or drive cables have a diameter, such as about 0.006 inch (about 0.15 millimeter.) In one embodiment, the braid can comprise four UHMWPE strands. The UHMWPE strands may be about 50 denier apiece. In other embodiments, the braid might comprise two strands, three strands, five strands, six strands, seven strands, eight strands, nine strands, ten strands, eleven strands, twelve strands, or greater than twelve strands of UHMWPE.

In one embodiment, the steering wires 42/52/62/72 can run along the inner diameter of the catheter to the distal end and are located within channels defined by an internal sleeve or liner. The liner can have a low coefficient of friction to facilitate the passage of devices through the catheter.

In an embodiment having four steering wires 42/52/62/72, the distal ends of said wires are arranged in paired fashion according to the spool to which they are attached. For instance, steering wires 42 and 52 are attached to first spool 20 and steering wires 62 and 72 are attached to second spool 120. Optimally, the distal ends of a pair of wires will be spaced at substantially 180 degree intervals around the circumference of the distal end of the catheter or endoscope to be steered. This allows the tip of the catheter to deflect in one direction when the steering wheel or apparatus to which they are attached is rotated in one direction and in the opposite when it is rotated in the opposite direction.

Figure 10:
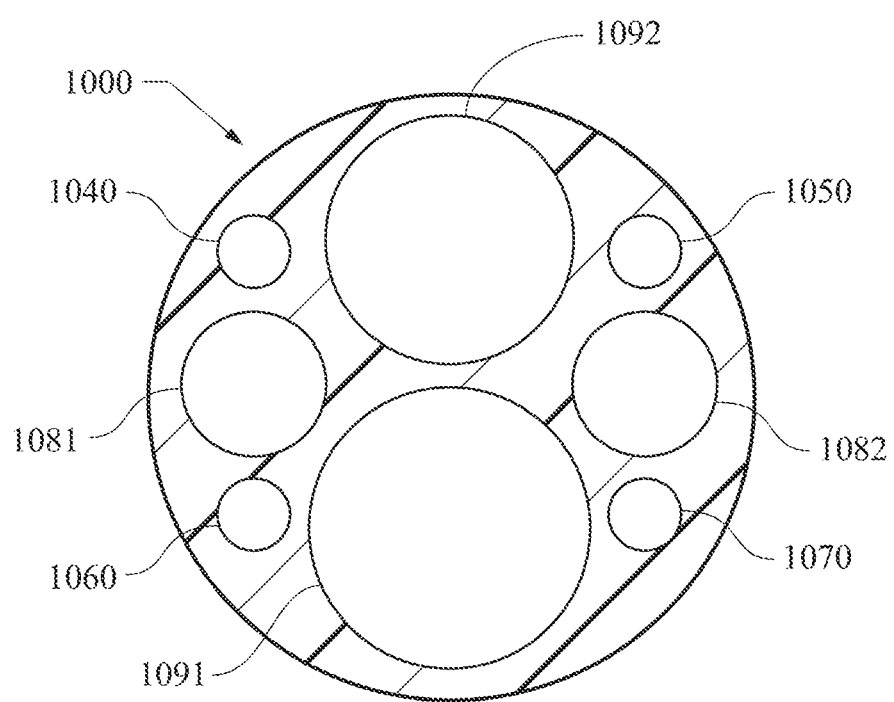
FIG. 10 is a radial cross-sectional view of a catheter in accordance with an embodiment.

Further, when four wires are present, optimally the spacing between wires will be 90 degrees, with the 180 degree spacing between wires of a single pair being maintained. A radial cross-section of an eight-lumen catheter 1000 having four steering wire lumens 1040/1050/1060/1070 is shown in FIG. 10. In this embodiment, the circumference of the distal end of the catheter 1000 (or an equivalent endoscope, which may be equipped with a distal visualization/imaging/light-capturing device such as a fiber optic camera, CCD, or CMOS) is compared to a clock face, and the distal end of steering wire 1042 which passes through lumen 1040 may be placed at 12 o'clock and its paired wire, steering wire 1052, would be placed at 6 o'clock. This permits deflection in the Y-plane when the steering wheel 1090 associated with the first pair of wires was engaged. The distal ends of third and fourth steering wires 1062/1072 could then be attached at the 3 o'clock and 9 o'clock positions and would then allow for deflection in the X-plane upon engagement of the second steering wheel 1092. Other lumens or channels provide further functions in this embodiment. For instance, channel 1081 may have a diameter of about double to about triple the diameter of the steering wire lumens 1040/1050/1060/1070 and may be able to allow passage of an optical fiber or other light source therethrough. Lumen 1082 may have substantially the same diameter as channel 1081 and may be a flushing channel allowing fluid to pass through it, or it may optionally allow for passage of a wire guide, or it may be configured to permit any number of functions as known in the art. Lumen 1092 may have a diameter of about triple to about six times the diameter of a steering wire lumen and may for instance be used as a camera channel. Lumen 1091 may be the largest channel in some embodiments, and may function as a working channel through which any surgical tool (forceps, scalpel, basket, and the like) may be passed. The diameter of lumen 1091 may be substantially the same as lumen 1092, or it may be somewhat larger.

Figure 4:
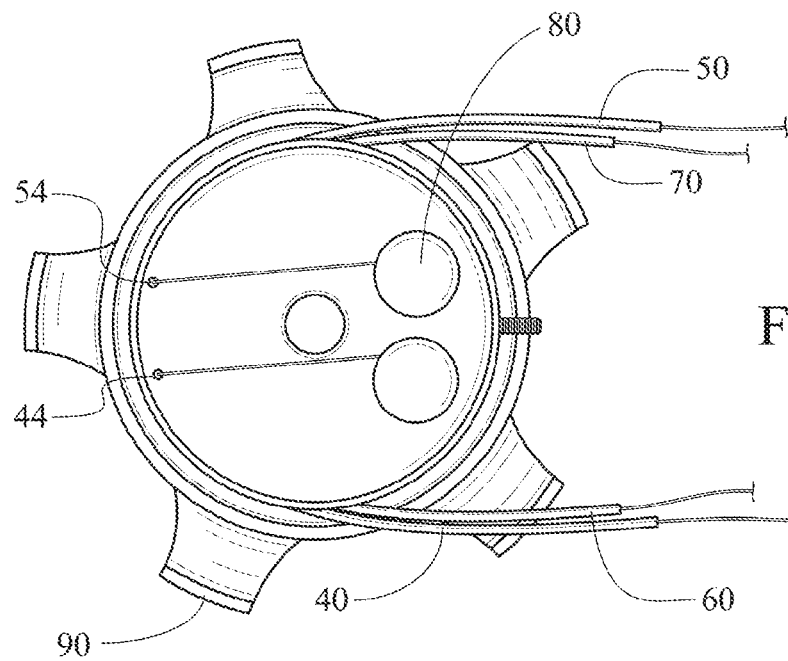
FIG. 4 is a top view of a rotation element and spool having a retaining tube in accordance with another embodiment.
Figure 5:
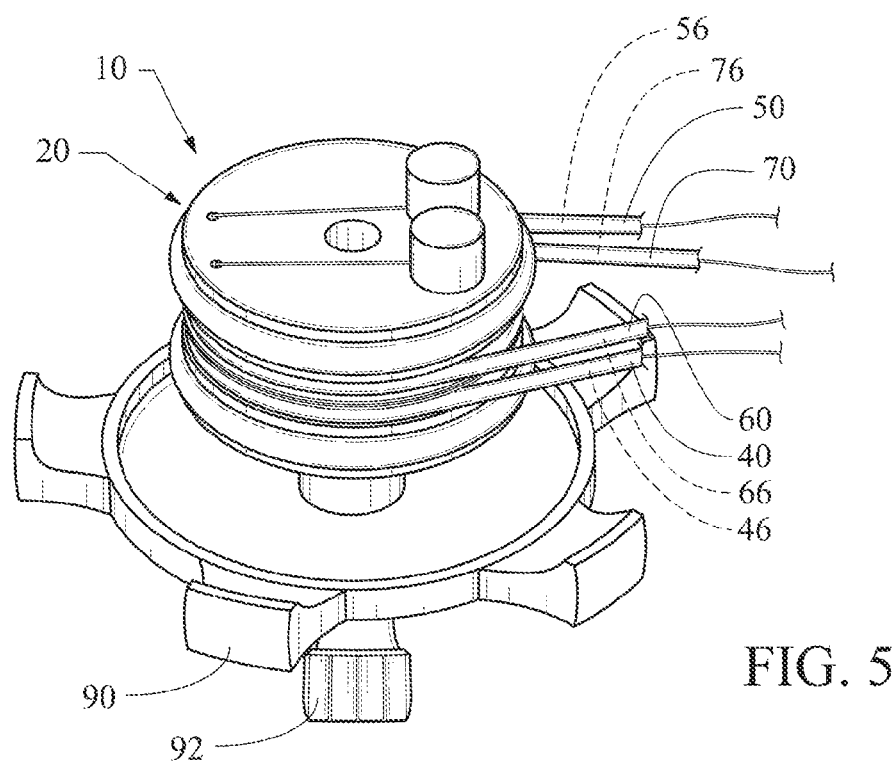
FIG. 5 is a perspective view of a rotation element and spool having a retaining tube in accordance with another embodiment.

Shown in FIGS. 3-5 are portions of a steering mechanism in accordance with another embodiment. Rather than the single spool 20 of the embodiment of FIG. 1-2, the steering mechanism of FIGS. 3-5 has two spools 20 in close proximity to one another. The first spool 20 has first and second tube halves 40 and 50 attached to its circumferential edge or groove 22. Second spool 120 has third and fourth tube halves 60 and 70 attached along circumferential edge 122. First, second, third, and fourth drive cables 42/52/62/72 pass into the lumens 46/56/66/76 of tube halves 40/50/60/70 in ways similar to those described above. In this embodiment, the presence of the retaining tube ensures that the drive cables will not slip off of the spool when they are passed through the lumens thereof. The drive cables optionally are attached, such as by tying and knotting, to knobs 80.

Each spool has an axle around which the spool is rotatable. These axles may be arranged concentrically around a single, coincident longitudinal axis. For instance, as shown in FIG. 3, first axle 30, attached to first spool 20, has a lumen running along its length and second axle 32 fits therethrough while attaching to second spool 120. First axle 30 and second axle 32 are rotatable independent of one another, allowing for deflection in a single plane if only one wheel 90 or 92 is turned, or in both planes if both are manipulated.

Each axle 30/32 has a steering wheel 90/92. In one embodiment, the controller is a user-operated rotatable wheel or knob that is adapted to pull and release the wires connected to the handle. When the catheter assembly or endoscope has two or more pairs of steering wires, the handle includes additional actuators and corresponding controls to drive the additional pairs of steering wires, as illustrated in FIG. 3-5. It will be appreciated that a three-spooled embodiment will have three axles and three wheels, a four-spooled embodiment will have four axles and four wheels, and so forth.

In one embodiment, the tube halves 40/50/60/70 represent individual tubes that are not interconnected. In another embodiment, the tube halves 40/50 and 60/70 are joined at the midpoint along the circumferential edge of the spool 20/120 to which they are attached to form a single tube assembly. The circumferential edges 22/122 of the spools 20/120 may have grooves formed along there lengths into which the tube halves 40/50/60/70 are inserted and attached. As depicted in FIG. 4-5, the top-down and perspective views illustrate the separate tube halves and the wires that extend from them. Such an arrangement prevents the drive cable from falling in the groove between, or on the outside of, the two spools 20/120.

As seen in FIGS. 6A-F and FIGS. 7-8, the handle has a proximal end 602, a distal end 604, and includes a controller or actuator by which a user can steer the distal end of the catheter. In the illustrated embodiment, the handle generally includes a portion of the lengths of the plurality of the steering wires of the assembly. To steer the catheter or endoscope, a user actuates the controller, which causes the wires to deflect. The deflection is caused by the user turning or pushing on one or both of the wheels 690 or 692. This causes a tensile force on the steering wires attached to the spool which shares an axle with the wheel. For instance, in an embodiment wherein retention tubes 640 and 650 are disposed on first spool 620, which is attached to axle 630, the first steering wheel 690 causes these wires to deflect. The lengths of the steering wires 642, 652, and 662 pass respectively through retention tubes 640, 650, and 660 (the wire through 670 is not shown) and then, distal of the spool assembly, through individual steering wire lumens formed in the body of the catheter or endoscope (where the wires are drawn as truncated for illustration simplicity, where those skilled in the art will appreciate that each extends to a distal connection/attachment within the body of the catheter or endoscope effective for manipulating/steering the distal end in a controlled manner).

By passing the steering wires 642/652 and 662, respectively, through the retention tubes 640/650 and 660/670, the steering wires do not slide off of the spool 620 or out of the groove in which they are placed. Further, dedicating individual steering wire lumens to each steering wire prevents tangling of the wires with one another or any other component of the device, and ensures that movement of the wires follows a defined path from the spool to the distal point of attachment to the catheter. In doing, so, turning the first and second steering wheels 690/692 forces the distal end of the catheter to deflect.

In an assembly such as in FIG. 10 wherein the steering wires are disposed at 90 degree intervals around the circumference of a circular device, in combination with a handle assembly as in FIG. 6, turning steering wheel 690 clockwise would cause deflection in the X plane, or left and right, and steering wheel 692 in the Y plane, or up and down. A clockwise turn of wheel 690 might cause retention tube 640 to move distally and retention tube 650 to move proximally, causing the distal end of the catheter to deflect to the right. A corresponding counterclockwise turn would then cause the opposite motion and result in the distal end of the catheter to deflect to the left. Independent of the motion of wheel 690, a clockwise turn of wheel 692 might cause retention tube 660 to move distally and retention tube 670 to move proximally, causing the distal end of the catheter to deflect in the upward direction. A counterclockwise turn of wheel 692 would cause downward deflection. This example is illustrative in nature and should not be interpreted as limiting the scope of the invention.

Figure 6A:
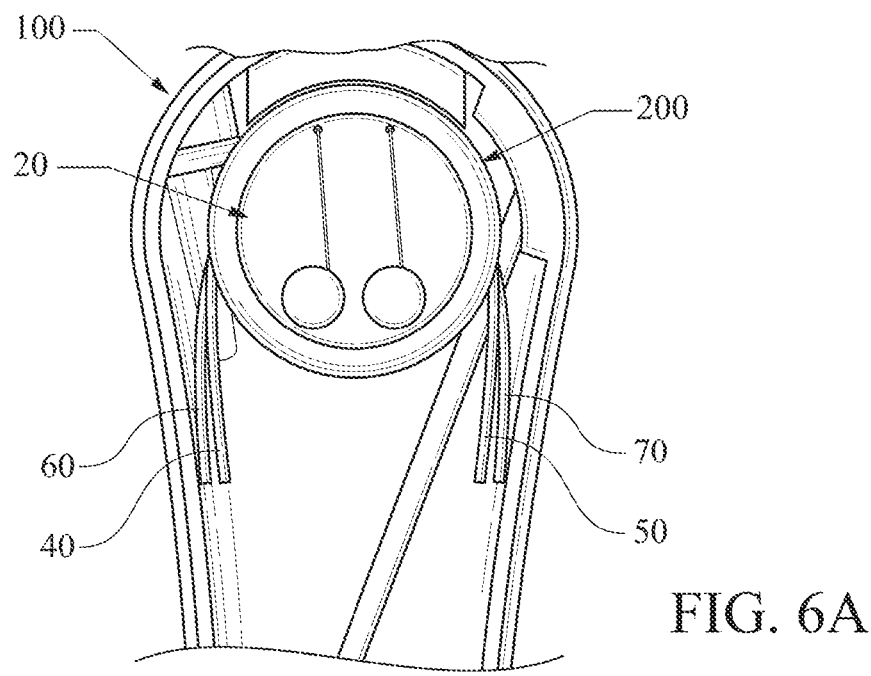
FIGS. 6A-F are perspective views of a rotation element and spool having a retaining tube and an associated housing in accordance with another embodiment.
Figure 7:
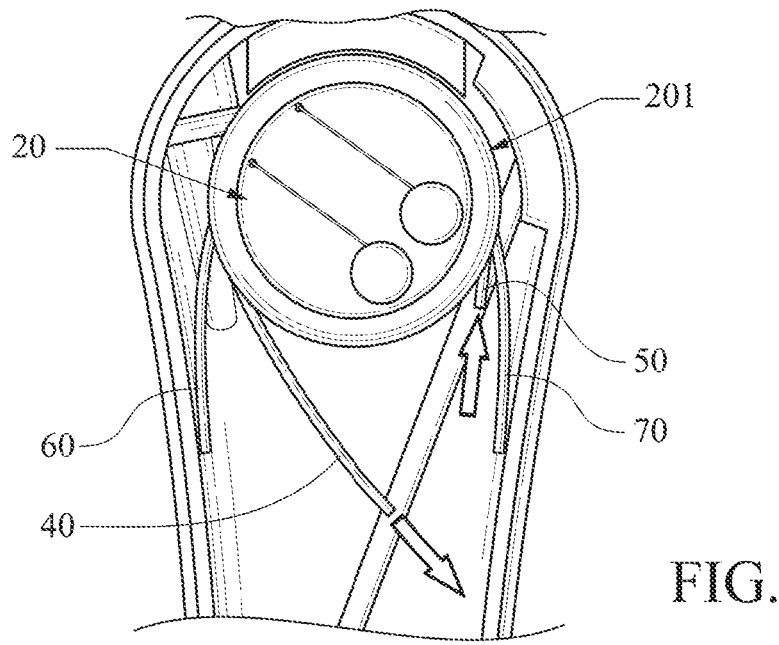
FIG. 7 is a top view of a rotation element and spool having a retaining tube in a second position in accordance with various embodiments.

The assembly inside of housing 100 as illustrated in FIG. 6A is shown in neutral position 200. In this position, the distal tip of the catheter or scope would not be deflected from its baked-in state. The assembly in FIG. 7 is shown in a first turned position 201 with a counter-clockwise rotation of first spool 20. Note that second spool 120 has not been rotated and as a consequence third tube half 60 and fourth tube half 70 can be seen in the same configuration as they were in FIG. 6. This counter-clockwise turn allows for a corresponding deflection in the distal end of the catheter. Likewise, in FIG. 8, the first spool 20 has been rotated clockwise from the neutral position 200 to attain a second turned position 202. This rotation propagates down the length of the catheter as an equal but opposite deflection of the distal time of the device.

The controller may take other forms, such as a rocker arm, mechanical slide, or rotatable lever, adapted to pull and release the wires. In one embodiment, the handle includes a locking mechanism, such that when a curve is activated by the controller, the curve may be locked in place.

Figure 8:
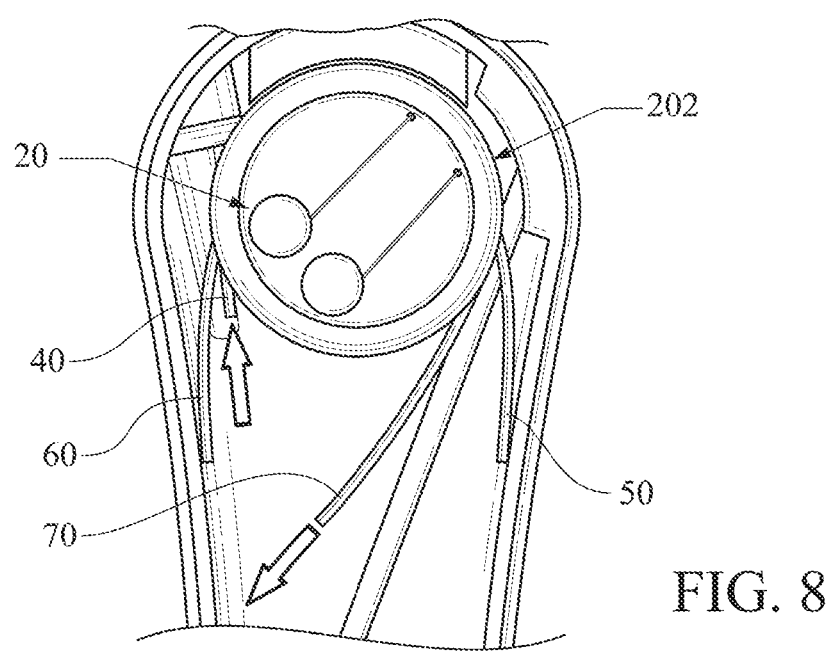
FIG. 8 is a top view of a rotation element and spool having a retaining tube in a second position in accordance with various embodiments.

In the illustrated embodiment shown in FIG. 6-8, the steering assembly includes two pairs of steering wires 42/52 and 62/72 that controllably steer the catheter in two perpendicular planes. In one embodiment, the catheter includes additional wires that allow a user to steer the distal end in multiple planes. In a further embodiment, the catheter only includes one control wire that allows the user to steer the distal end in one direction. The center of both lumens and both coils lie on the Y-axis to provide less resistance against deflection in the X-plane.

In some embodiments, the catheter can include a pair of steering wires that allow the user to steer the distal tip in a single plane. In another embodiment, the catheter may only include one steering wire that allows the user to steer the distal tip in one or two directions.

Figure 6B:
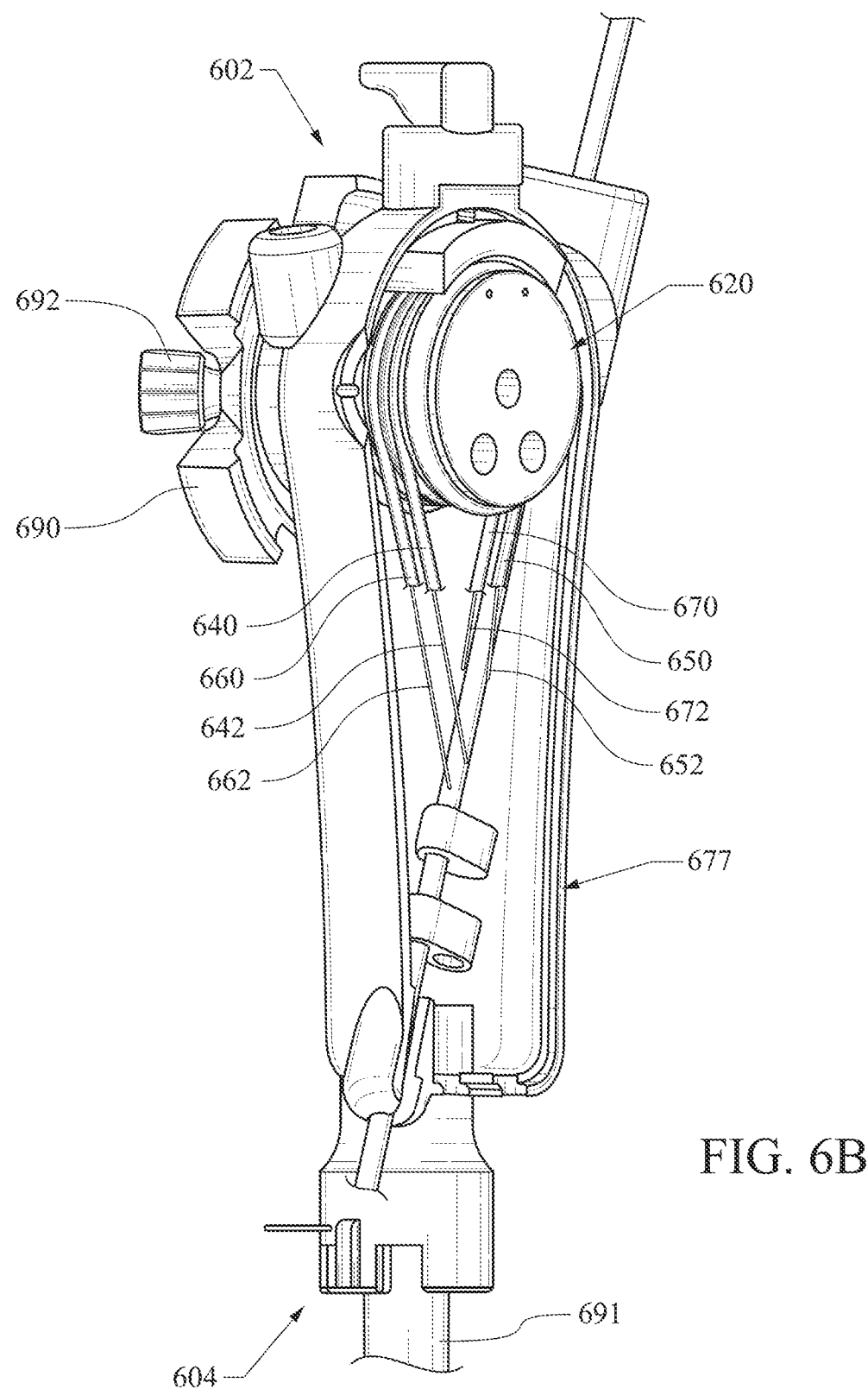
Figure 6C:
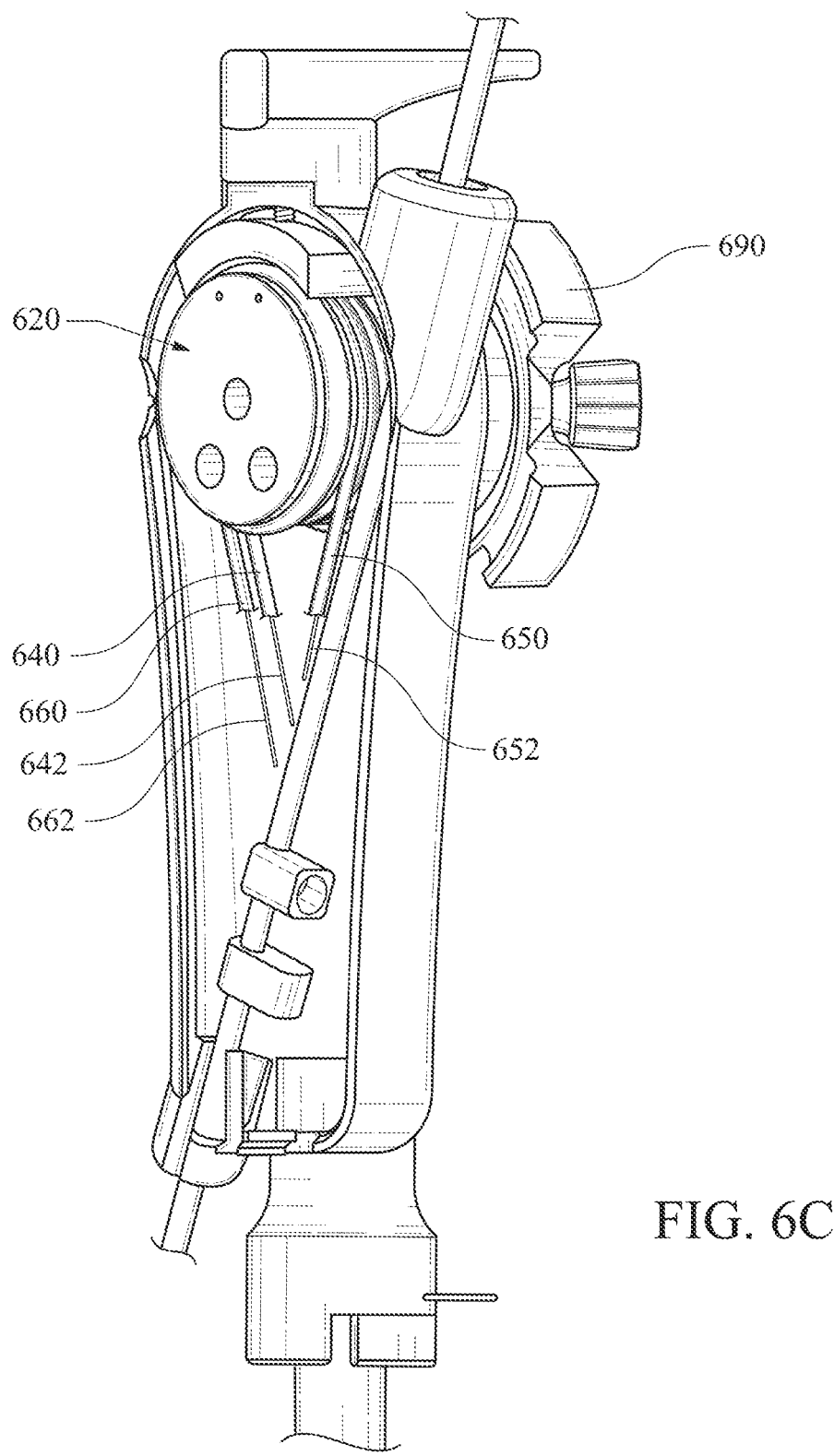
Figure 6D:
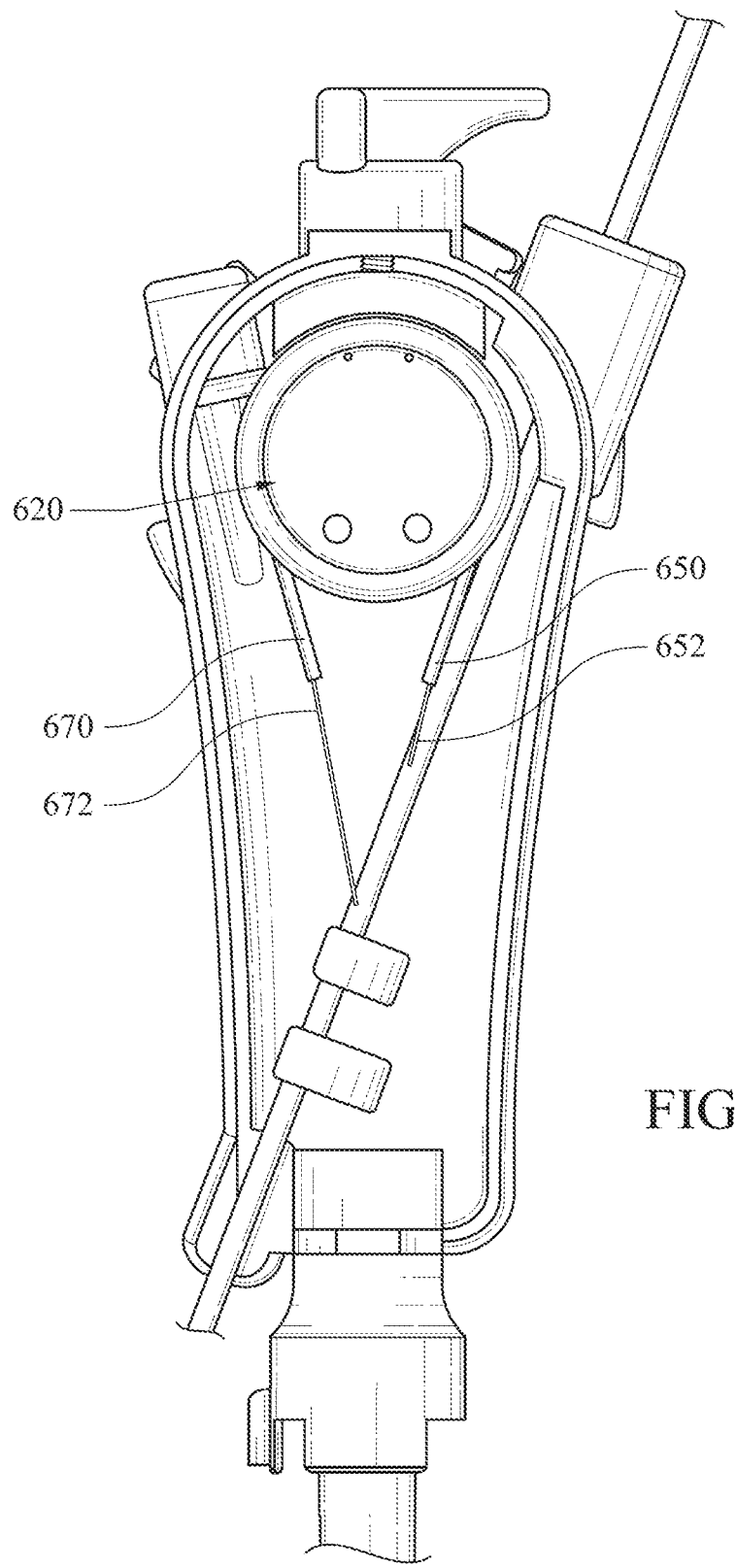
Figure 6E:
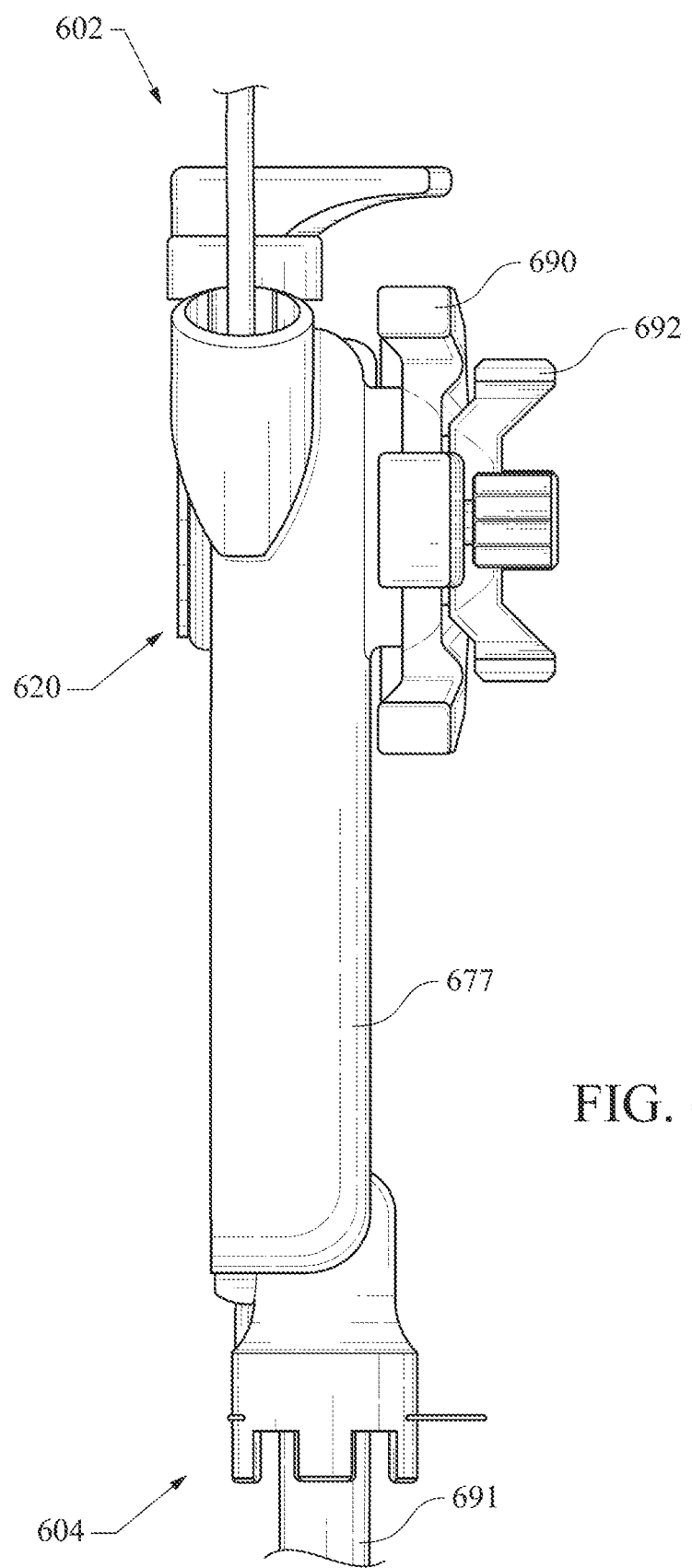
Figure 6F:
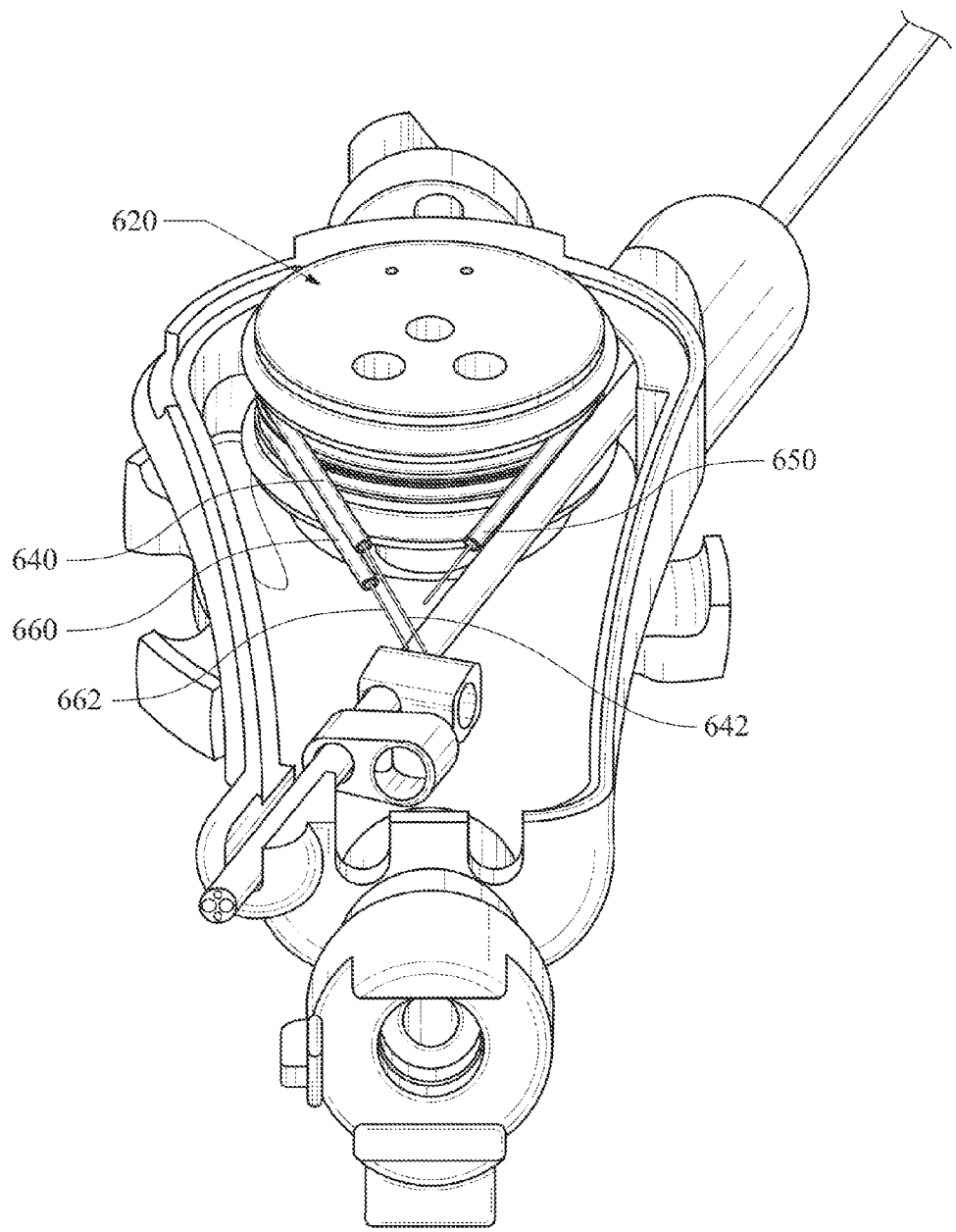

The first steering element or wheel 90/690 for up and down bending control is rotatably fitted over the second axle for independent rotation with respect to the second steering element or wheel 92/692. The first steering element 90/690 is integrally formed or keyed for rotation with one end of a first axle 30. The first axle 30 is concentrically arranged in a rotational manner over the second axle. The opposite end of the first axle 30 extends outside the handle housing to which the control knob is attached for co-rotation. A structure may be provided that rotatably supports the wheels and axles within the handle housing 677. As seen in FIG. 6E, the housing 677 surrounds and encloses the entire spool and steering wire assembly. A catheter 691 or endoscope is attached to the housing 677 at the distal end 604 of the handle.

An endoscope or catheter with such a steering assembly can be used for a variety of applications. In one use, the endoscope is inserted down the esophagus of a patient and advanced through the stomach and into the duodenum to the approximate location of the entrance to the common bile duct or papilla. After positioning the endoscope adjacent the common bile duct entrance, the catheter of the catheter assembly is advanced past the distal end of the endoscope and into the common bile duct entrance. Alternatively, the catheter may be routed prior to endoscope insertion. Once inside the common bile duct, the fiberscope allows a physician to view tissue in the bile duct, pancreatic duct and/or intrahepatics for diagnosis and/or treatment.

The endoscope can be passed through the stomach and into the duodenum at the bottom of the stomach. The biliary tree comprises the cystic duct from the gall bladder, the hepatic duct from the liver and the pancreatic duct from the pancreas. Each of these ducts joins into the common bile duct. The common bile duct intersects with the duodenum a slight distance below the stomach. The papilla controls the size of the opening at the intersection between the bile duct and duodenum.

Once advanced into the common bile duct, a fiber optic cable of the viewing device located within the catheter allows a physician to view tissue in the bile duct for diagnosis and/or treatment. In use, the tip of the catheter is advanced beyond the end of the endoscope and is steered in the direction of the papilla. The guide wire is then advanced through the papilla and the catheter is advanced to cannulate the papilla. Once in the biliary tree, and with visualization provided via the fiberscope or other viewing device, further diagnostic or curative procedures for which the catheter assembly has been adapted can be initiated.

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment of the invention.

I claim:

1. A medical device with a proximal end and a distal end including a steering mechanism nearer the proximal than the distal end, the steering mechanism comprising:
    a first spool having a first circumferential groove, the first spool being rotatable about a first rotation axis that extends through a radial center of a first spool face;
    a second spool having a second circumferential groove, the second spool being rotatable about a second rotation axis that is coaxial with the first rotation axis and that extends through a radial center of a second spool face;
    a first retaining tube including a lumen extending longitudinally therethrough, a first end and second end with a middle length therebetween; a portion of the middle tube length of the first retaining tube being disposed in the first circumferential groove;
    a second retaining tube including a lumen extending longitudinally therethrough, a first end and second end with a middle length therebetween; a portion of the middle length of the second retaining tube being disposed in the second circumferential groove;
    a first drive cable disposed through a length of the lumen of the first retaining tube and extending distally from the first end of the first retaining tube, a second drive cable disposed through a length of the lumen of the second retaining tube and extending distally from the first end of the second retaining tube, a third drive cable disposed through a length of the lumen of the first retaining tube and extending distally from the second end of the first retaining tube, and a fourth drive cable disposed through a length of the lumen of the second retaining tube and extending distally from the second end of the second retaining tube;

wherein the first spool and the second spool are rotatable independent of one another, wherein a proximal end length of each of the first and third drive cables contacts the first spool face and a proximal terminal end of each of the first and third drive cables being directly attached to the first spool by a knob, and wherein a proximal end length of each of the second and fourth drive cables contacts the second spool face and a proximal terminal end of each of the second and fourth drive cables being directly attached to the second spool by a knob.

2. The medical device of claim 1 wherein a proximal terminal end of at least one of the drive cables is attached to at least one of the spools with a knob.

3. The medical device of claim 1 wherein a proximal terminal end of each of the drive cables is attached to at least one of the spools with a knob.

4. The medical device of claim 1 wherein the first end and the second end of the first retaining tube, and the first end and the second end of the second retaining tube each extend generally distally from the spools.

5. The medical device of claim 1, further comprising a multilumen tubular body extending distally relative to the spools, wherein each drive cable extends into a separate one of the lumens of the multilumen tubular body.

6. The medical device of claim 5, wherein the multilumen tubular body comprises a catheter, an endoscope, or both.

7. The medical device of claim 5, where, within the lumens of the multilumen tubular body, the first drive cable is substantially 180 degrees away from the second drive cable, the third drive cable is substantially 180 degrees away from the fourth drive cable, or both.

8. The medical device of claim 1 wherein the drive cables are disposed at least partially through the retaining tubes in a manner that effectively prevents the drive cables from entangling when one or both spools is rotated about the rotation axis of said spool.

9. The medical device of claim 8 wherein a proximal end portion of each of the drive cables exits through the retaining tube being a corresponding retaining tube through which that drive cable passes and engages a knob mounted into the spool around which the corresponding retaining tube is disposed.

* * * * *